US012788476B2

(12) United States Patent
Koltz, Jr.

(10) Patent No.: US 12,788,476 B2
(45) Date of Patent: Nov. 10, 2026

(54) POWER CONTROL FOR AN ELECTROSURGICAL VESSEL SEALER

(71) Applicant: Conmed Corporation, Largo, FL (US)

(72) Inventor: Michael L. Koltz, Jr., Aurora, CO (US)

(73) Assignee: Conmed Corporation, Largo, FL (US)

( * ) Notice: Subject to any disclaimer, the term of this patent is extended or adjusted under 35 U.S.C. 154(b) by 847 days.

(21) Appl. No.: 17/783,907

(22) PCT Filed: Dec. 11, 2020

(86) PCT No.: PCT/US2020/064436
§ 371 (c)(1),
(2) Date: Jun. 9, 2022

(87) PCT Pub. No.: WO2021/119387
PCT Pub. Date: Jun. 17, 2021

(65) Prior Publication Data
US 2023/0017125 A1 Jan. 19, 2023

Related U.S. Application Data

(60) Provisional application No. 62/947,555, filed on Dec. 13, 2019.

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00642* (2013.01);
(Continued)

(58) Field of Classification Search
CPC .. A61B 2018/0063; A61B 2018/00642; A61B 2018/00702; A61B 2018/00875;
(Continued)

(56) References Cited

U.S. PATENT DOCUMENTS

2011/0319882 A1* 12/2011 Kennedy ............ A61B 18/1482 606/33
2015/0119870 A1* 4/2015 Rudie ................ A61B 18/1815 606/33
2021/0100606 A1* 4/2021 Zhao ........................ G06N 3/09

FOREIGN PATENT DOCUMENTS

EP 3207890 A1 8/2017
WO WO2011156310 A1 12/2011
WO WO2017003855 A1 1/2017

OTHER PUBLICATIONS

International Search Report Form PCT/ISA/220, International Application No. PCT/US2020/064436, pp. 1-10, Dated Dec. 11, 2020.

* cited by examiner

*Primary Examiner* — Bradford C. Blaise
(74) *Attorney, Agent, or Firm* — Bond, Schoeneck & King, PLLC; David L. Nocilly

(57) ABSTRACT

A power delivery approach for delivering power to an electrosurgical vessel sealer when the jaws of the sealer surround tissue to be desiccated. Power delivery commences at a starting point that is at least 40 Joules and then decreases over a first predetermined period of time to a predetermined minimum power level to provide approximately 15 Joules in total. When the predetermined minimum power level is reached, power is then continuously increased over a second predetermined period of time to fully desiccate the tissue. Power delivery is terminated prior to over-desiccation of the tissue.

17 Claims, 8 Drawing Sheets

(52) U.S. Cl.
CPC ............... *A61B 2018/00702* (2013.01); *A61B 2018/00875* (2013.01); *A61B 18/1442* (2013.01)

(58) Field of Classification Search
CPC ............ A61B 18/1442; A61B 18/1445; A61B 2018/145
See application file for complete search history.

POWER CONTROL FOR AN ELECTROSURGICAL VESSEL SEALER

CROSS-REFERENCES TO RELATED APPLICATIONS

This application is a national stage application under 35 U.S.C. 371 based on international patent application PCT/US20/64436 filed on Dec. 11, 2020, which claims priority to U.S. Provisional Patent Application Ser. No. 62/947,555, filed on Dec. 13, 2019 and entitled "POWER CONTROL FOR AN ELECTROSURGICAL VESSEL SEALER," the entireties of which are incorporated herein by reference.

BACKGROUND OF THE INVENTION

1. Field of the Invention

The present invention relates surgical instruments and, more specifically, to a electrosurgical vessel sealer having an improved power delivery.

2. Description of the Related Art

Electrosurgical vessel sealers are surgical instruments that are used for the occlusion of blood vessels and halting of bleeding during surgical procedures. The electrodes of the vessel sealer are carried by a pair of opposing jaws and interconnected to an electrosurgical generator that can selectively supply radiofrequency (RF) energy to the electrodes. A user may close the jaws around a vessel to be sealed by squeezing a lever associated with a handle assembly. The vessel may then be sealed by supplying the RF energy to the clamped vessel.

Electrical power control of the vessel sealer is controlled by the electrosurgical generators. Conventional approaches to power control involve the application of power according to a predetermined power curve where power is variably applied to have a particular impact on the tissue to be sealed. Conventional power curves often have extended vessel sealing times and are associated with energy lost to the jaws and the environment, which can cause sticking of tissue to the vessel sealer and charring of tissue. Accordingly, there is a need in the art for a power delivery approach that is more efficient and thus can employ lower temperatures that involve less tissue sticking and charring.

BRIEF SUMMARY OF THE INVENTION

The present invention provides a more efficient approach for sealing vessels that shortens vessel sealing time with a higher fraction of thermal energy remaining in the vessel and thus less energy loss to jaws and environment. The present invention includes an electrosurgical system having a vessel sealer having a pair of jaws and an electrosurgical generator coupled to the pair of jaws of the vessel sealer and configured to output radiofrequency energy to the vessel sealer according to a predetermined continuous power curve. The predetermined continuous power curve comprises a first power delivery segment that commences at a first power level and continuously decreases to a second power level and a second power delivery segment that commences with the second power level and increases to a final power level. The first power delivery segment occurs during a time period of between 0.250 and 9.75 seconds, and optimally about 0.750 seconds. The second power delivery segment occurs during a time period of between 0.250 and 9.75 seconds, and optimally about 4.25 seconds. The first power delivery segment delivers an amount of power that will not cause any tissue trapped in the pair of jaws to reach a temperature that results in boiling of any moisture in the tissue. The first power delivery segment delivers an amount of power that causes any tissue trapped in the pair of jaws to desiccate. The final power level will not cause over-desiccation of any tissue trapped in the pair of jaws. The second power delivery segment ends when any tissue in the pair of jaws has an impedance that exceeds a predetermined value. The first power delivery segment has a shape selected from the group consisting of linear, concave, convex, and combinations thereof. The second power delivery segment has a shape selected from the group consisting of linear, concave, convex, and combinations thereof. The first power delivery segment comprises an exponential decay curve and the second power delivery segment is linear.

The present invention also includes a method of controlling the power output from an electrosurgical generator to a vessel sealer having a pair of jaws. The method includes the steps of providing the vessel sealer having the pair of jaws, coupling the electrosurgical generator to the pair of jaws of the vessel sealer, and powering the electrosurgical generator to output radiofrequency energy to the vessel sealer according to a predetermined continuous power curve. The predetermined continuous power curve comprises a first power delivery segment that commences at a first power level and continuously decreases to a second power level and a second power delivery segment that commences with the second power level and increases to a final power level.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
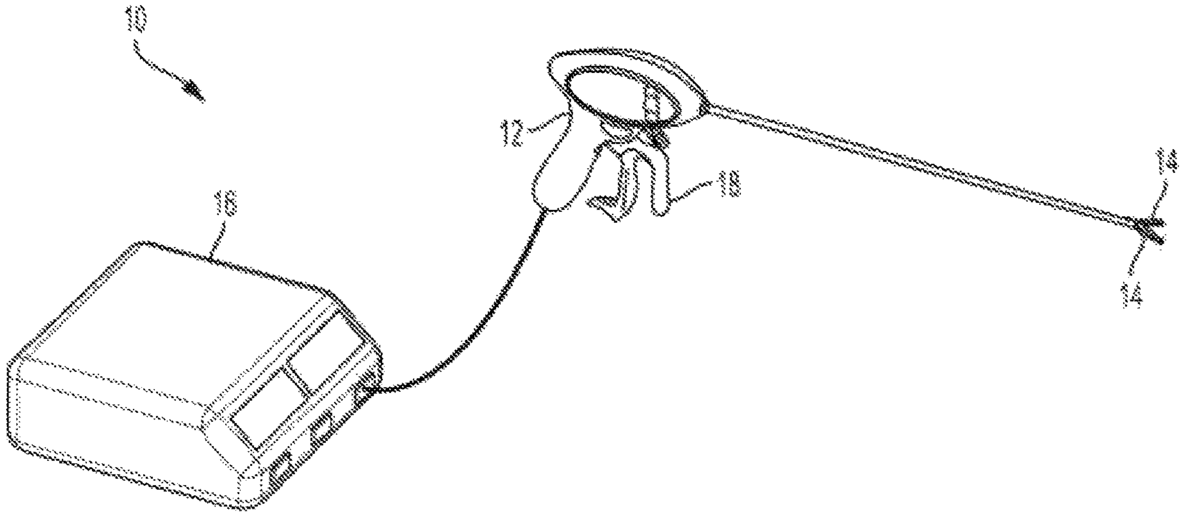
FIG. 1 is a perspective view of an electrosurgical system according to the present invention

Referring to the figures, wherein like numeral refer to like parts throughout, there is seen in FIG. 1 an electrosurgical system 10 comprising a vessel sealer 12 having a pair of conductive opposing jaws 14 that are interconnected to an electrosurgical generator 16 that can supply RF energy to electrodes of jaws 14 for the desiccation of a blood vessel trapped between jaw 14. The dimensions of jaws 14 and the type of RF energy supplied will produce desiccation of the blood vessel in a region of a particular width as determined by the thermal spread of the energy being supplied to the blood vessel. As is known in the art, jaws 14 are pivotally mounted to vessel sealer 12 for movement between an open position and a closed position in response to a user operating a lever 18 extending from the main body 20 of sealer 12.

Figure 2:
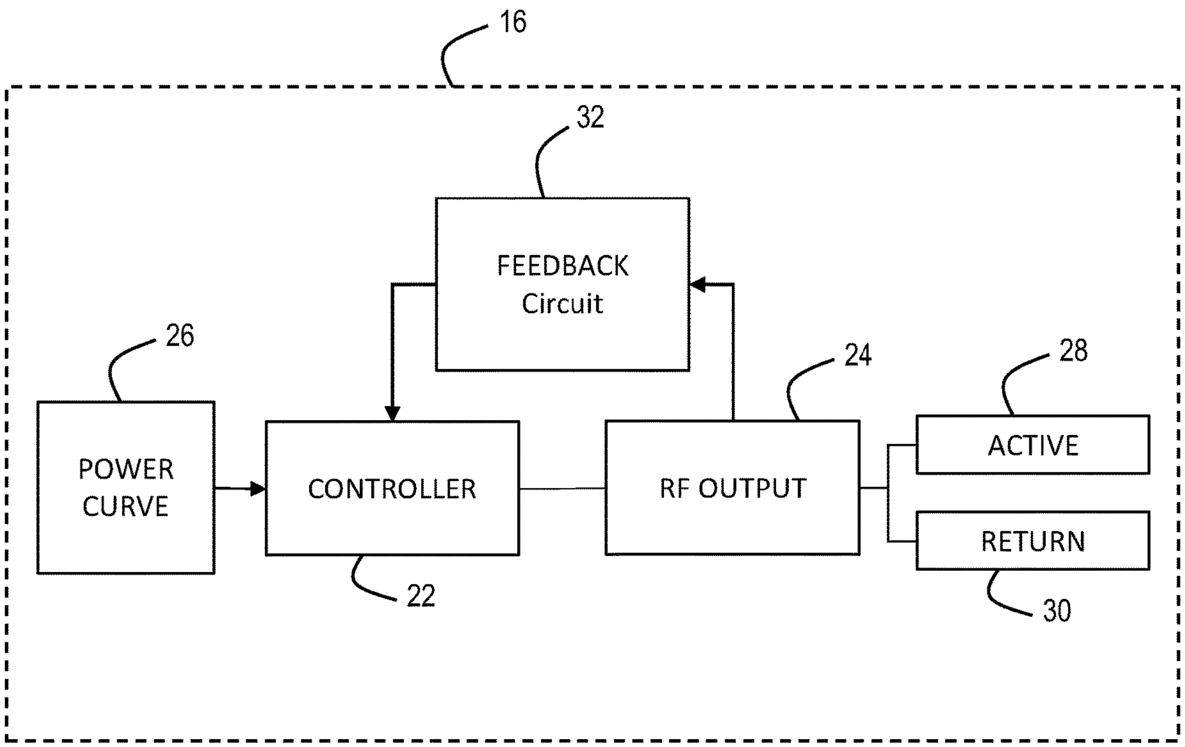
FIG. 2 is a schematic of an electrosurgical generator for an electrosurgical system that may be configured to deliver power according to the present invention.

Referring to FIG. 2, electrosurgical generator 16 comprises the electronics and circuitry response for precisely delivering RF energy to jaws 14 according to the present invention. The components, connections, sensing elements, electrical circuits, power source, user controls, and programmable control elements of electrosurgical generator 16 are known in the art and only discussed herein with respect to the specific aspects of electrosurgical generator 16 that are configured for implementation of the present invention. More specifically, electrosurgical generator 16 comprises a controller 22 that is programmed to execute substantially all of the feedback and regulation functionality of electrosurgical generator 16 and, more specifically, output radiofrequency energy from an RF output 24 according to one or more predefined power delivery curves according to the present invention that are stored in a power curve module 26. RF output 24 is coupled to an active path 28 and a return 30 of electrosurgical generator 16 that may be coupled to an electrosurgical instrument, such as vessel sealer 12, to deliver radiofrequency according to one or more of the power delivery curves to jaws 14 and thus desiccation of any tissue trapped within jaws 14. Electrosurgical generator 16 includes feedback circuit 32 so that controller 22 can monitor the output of radiofrequency energy from RF output 24. As is known in the art, feedback information provided by feedback circuit 32 can be used by controller 22 to control, regulate, and adjust the delivery of radiofrequency according to one or more of the power delivery curves, and to monitor the amount of power delivered to vessel sealer 12 over time.

Figure 3:
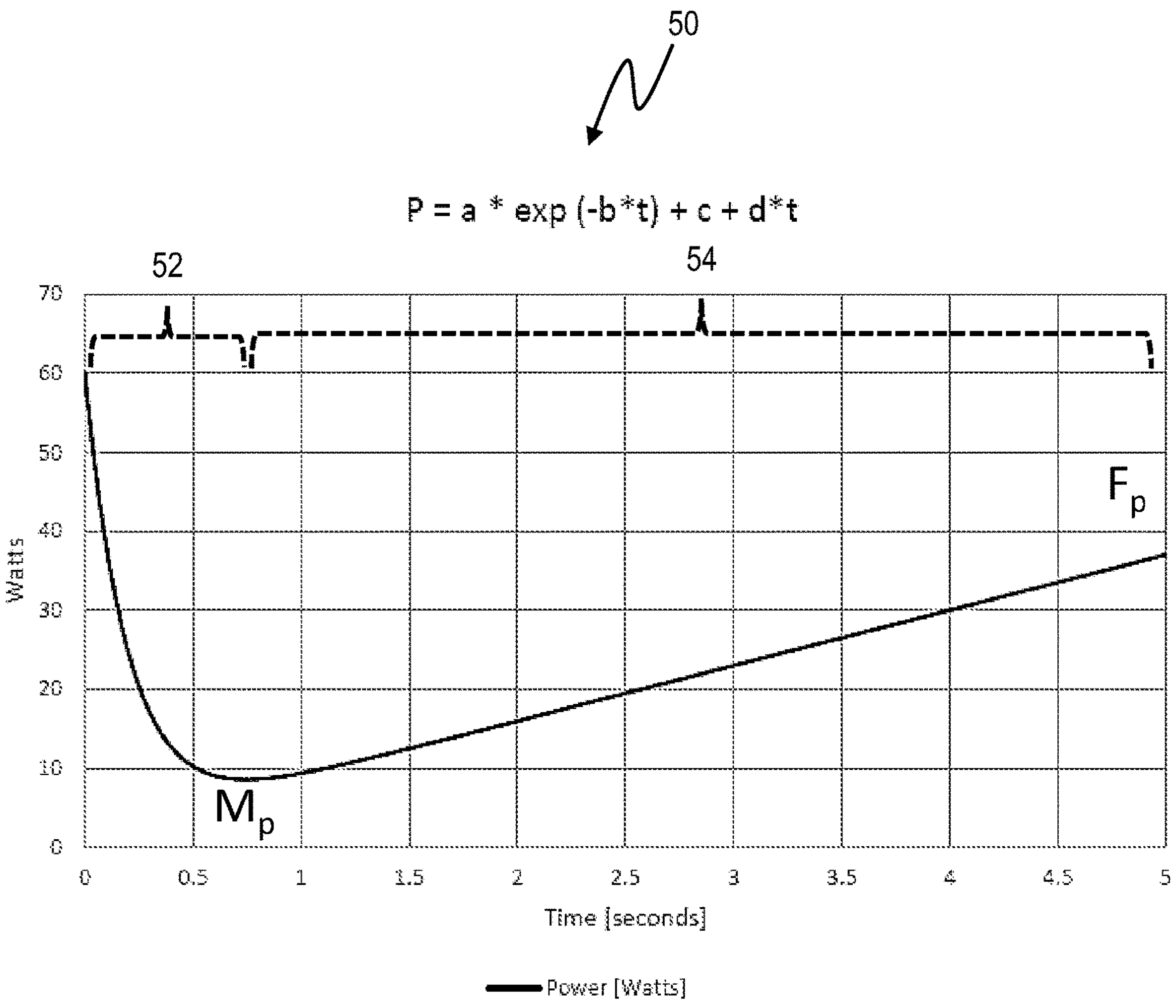
FIG. 3 is a power delivery curve according to an embodiment the present invention.

Referring to FIG. 3, electrosurgical generator 16 is programmed to output power to jaw 14 according to a power delivery curve 50 of the present invention to accomplish a sealing cycle where tissue held between the jaws is fully desiccated. More specifically, power delivery curve 50 for the sealing cycle involves the delivery of power over time according to a first power delivery segment 52 and then a second power delivery segment 54. First power delivery segment 52 commences at a power level of at least 40 Watts and then the power level is continuously decreased to a predetermined non-zero minimum power $M_p$ over a time period of between 0.250 and 9.75 seconds, and optimally about 0.750 seconds. First power delivery segment 52 is configured to generate a quantity of energy sufficient to raise the temperature of the inherent thermal mass of the electrodes and jaw components without raising the temperature of the tissue to its boiling point. First power delivery segment 52 may be configured so that the energy quantity of first power delivery segment 52 is optimized for the smallest vessel and thinnest tissues expected to be sealed in a surgical procedure. The nominal value of the energy quantity for first power delivery segment 52 is fifteen (15) Joules, but can range between 1 and 50 Joules depending on the circumstances.

Second power delivery segment 54 commences when the predetermined non-zero minimum power $M_p$ is reached, and thus first power delivery segment 52 has ended. Second power delivery segment 54 involves a continuous increase in the power level over a predetermined period of time until a predetermined final power level $F_p$ is reached. Second power delivery segment 54 commences at predetermined non-zero minimum power $M_p$ a power and increases to final power level $F_p$ over a time period of between 0.250 and 9.75 seconds, and optimally about 4.25 seconds. Second power delivery segment 54 is intended to deliver sufficient energy to vessels to desiccate tissue but terminate prior to over-desiccation of the tissue. Over-desiccation can be observed as burning, excessive thermal spread, and low vessel burst pressures. Tissues having lower masses will need to terminate sooner than those with greater mass. Final power level $F_p$ is selected to provide desiccation of tissue without any charring. The gradually increasing nature of second power delivery segment 54 precludes over-desiccation of smaller tissue masses, which generally comprise vessels smaller than 3 millimeters in diameters as well as thin connective tissues, while larger tissue masses comprise vessels of 7 millimeters in diameter and greater. Termination of second power delivery segment 54, and thus the entire power control cycle 50, occurs when the detected tissue impedance exceeds a threshold value.

Figure 4:
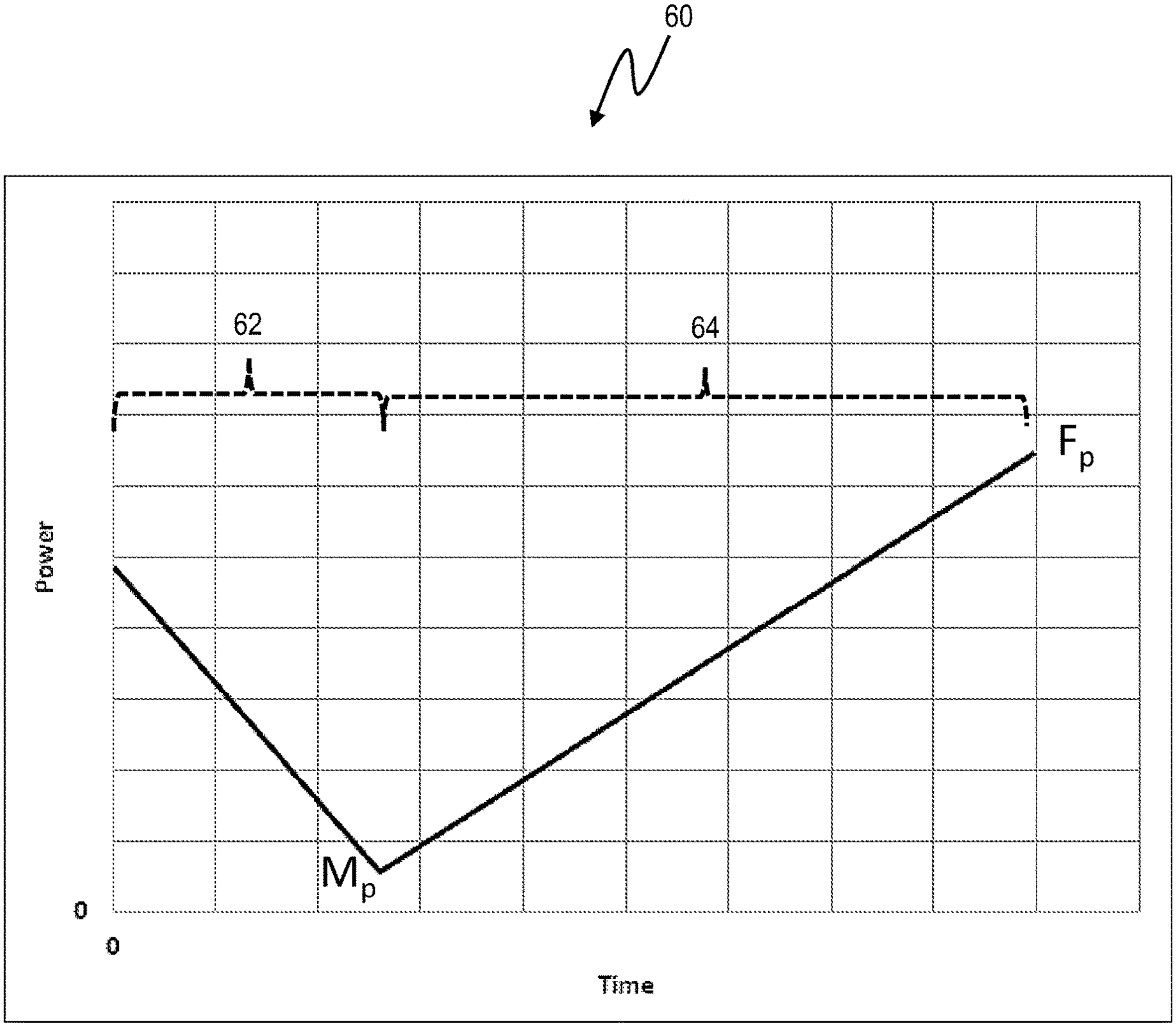
FIG. 4 is a power delivery curve according to another embodiment of a power control algorithm of the present invention.
Figure 5:
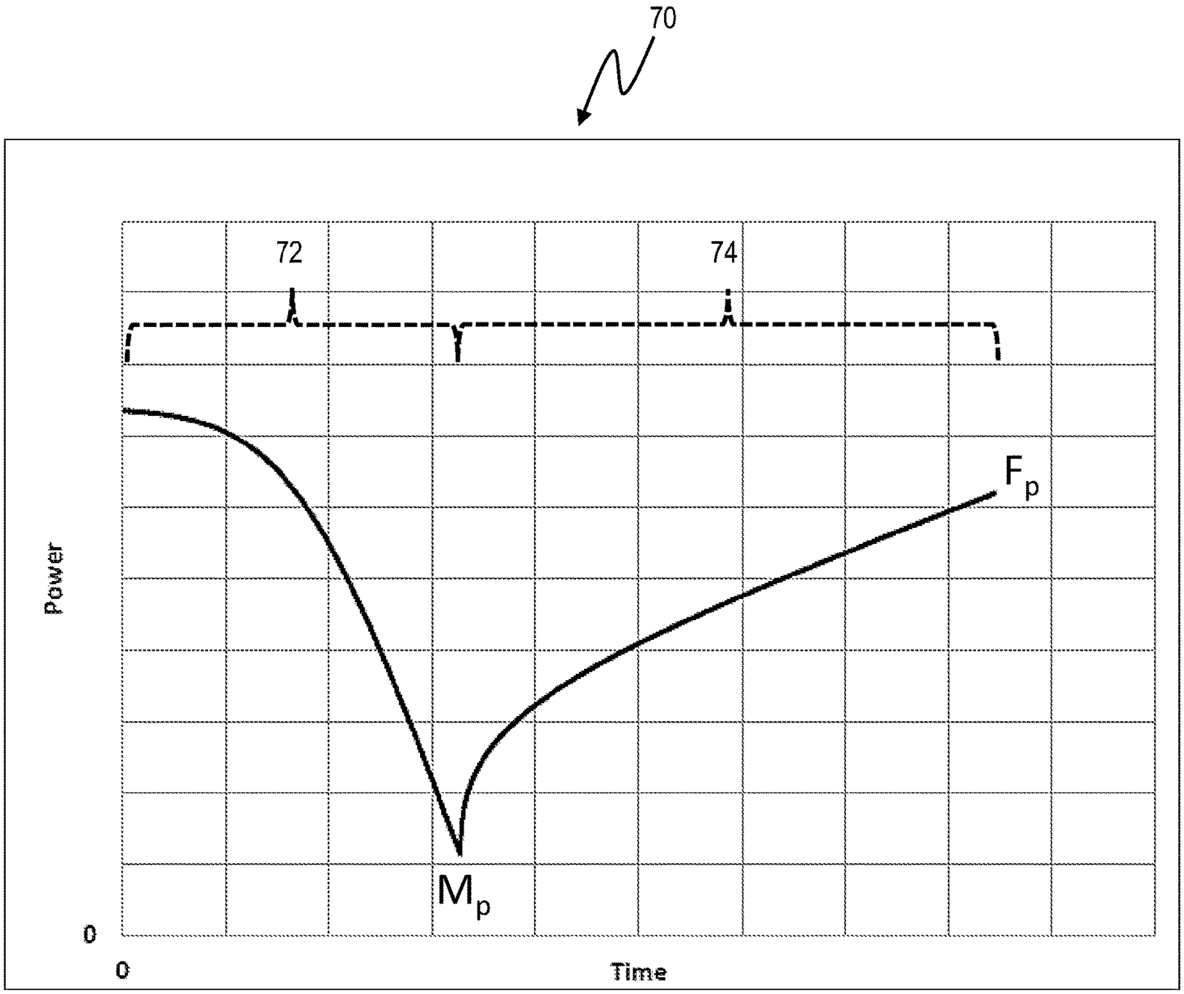
FIG. 5 is a power delivery curve according to a further embodiment of a power control algorithm of the present invention.
Figure 6:
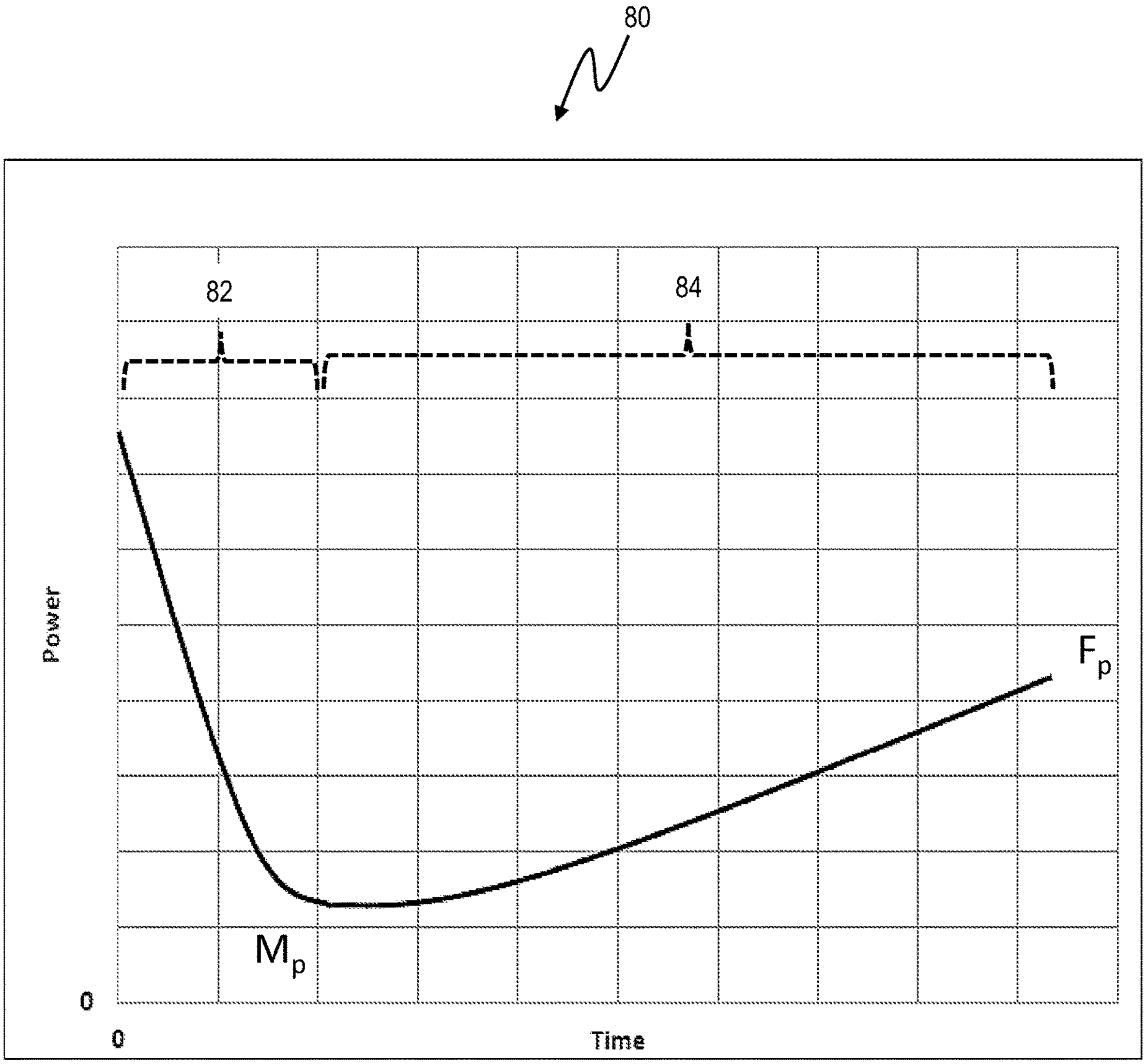
FIG. 6 is a power delivery curve according to an additional embodiment of a power control algorithm of the present invention.
Figure 7:
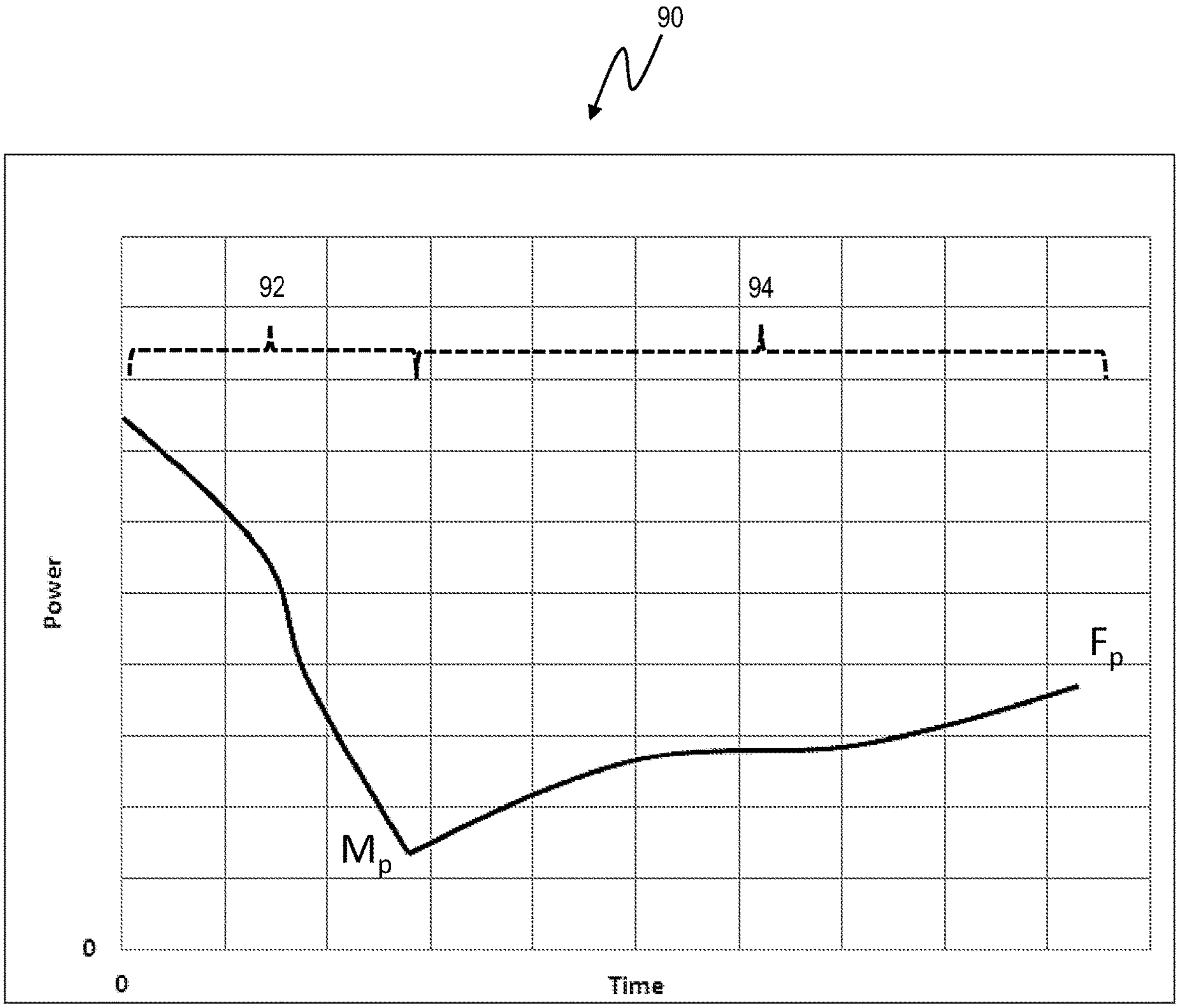
FIG. 7 is a power delivery curve according to yet another embodiment of a power control algorithm of the present invention.

The power delivered according to the algorithm is continuous, non-constant, non-switching, and non-pulsed. Referring to FIG. 3, the overall shape of each of first power delivery segment 52 and second power delivery segment 54 can be linear, concave, convex, or combinations thereof. For example, as seen in FIG. 3, first power delivery segment 52 can approximate an exponential decay curve while second power delivery segment 54 is generally linear. The rates of change of first power delivery segment 52 and second power delivery segment 54 of power cycle 50 are fixed throughout the sealing cycle in the embodiment of FIG. 3, but may be varied throughout the sealing cycle, as seen in the embodiments of FIGS. 4 through 6, illustrating power control cycle 50 variations having power delivery segment 62 and second power delivery segment 64, power delivery segment 72 and second power delivery segment 74, and power delivery segment 82 and second power delivery segment 84, and power delivery segment 92 and second power delivery segment 94, In a further embodiment, tissue impedance may be used to set the rate of change of first power delivery segment 52 and second power delivery segment 54. In another embodiment, the rates of change of first power delivery segment 52 and second power delivery segment 54 may be set according to the rate of change of tissue impedance.

Figure 8:
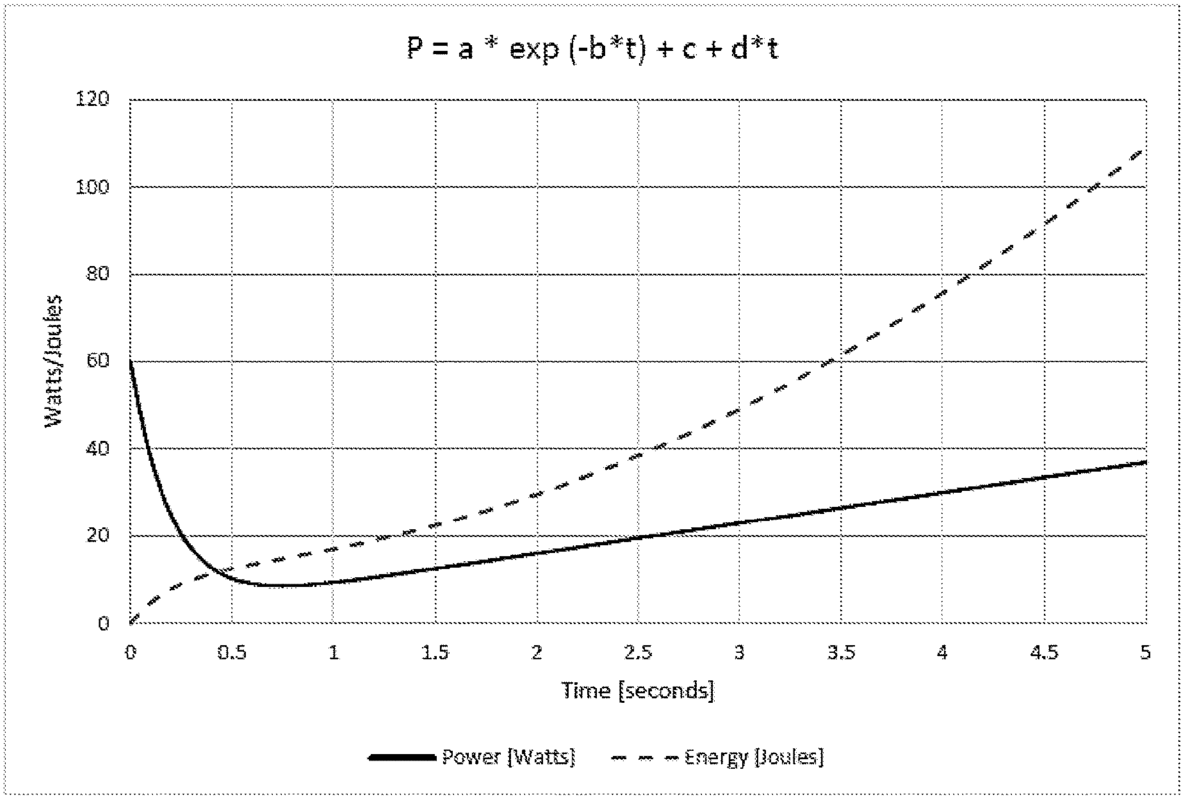
FIG. 8 is a graph of the energy plot superimposed over a power delivery curve according to an embodiment of a power control algorithm of the present invention.

Referring to FIG. 8, the transfer function for power delivery curve 50 is expressed as $P=A\times e^{-B\cdot t}+C+D\cdot t$, where P is the power level, t is the time since initiation of the sealing cycle, A is a constant used to influence the maximum power level, B is a constant used to influence the rate of decay of first segment 52, C is a constant used to influence the minimum power level, and D is a constant used to influence the rate of increase of second segment 54. The power transfer function can be integrated with respect to time to yield the energy delivered:

$$E = \frac{-A}{B}\cdot e^{-B\cdot t} + C\cdot t + \frac{D}{2}\cdot t^2 + \frac{A}{B}$$

As a first example, electrosurgical generator 16 providing power according to first power delivery segment 52 will deliver approximately 15 Joules of energy within a period of 100 to 1500 milliseconds after sealing cycle initiation. First power delivery segment 52 initiates when between 1 and 50 Joules of energy has been delivered. First power delivery segment 52 and second power delivery segment 54 will typically deliver a total energy of 90 Joules and terminate within 2 to 10 seconds after sealing cycle initiation.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. An electrosurgical system, comprising:

a vessel sealer having a pair of jaws; and an electrosurgical generator coupled to the pair of jaws of the vessel sealer and configured to output radiofrequency energy to the vessel sealer according to a predetermined continuous power curve;

wherein the predetermined continuous power curve starts with a first power delivery segment that commences at a first power level and continuously decreases to a predetermined second, non-zero power level and then continues with a second power delivery segment that commences with the second, non-zero power level and increases to and ends at a final power level that is greater than the predetermined second, non-zero power level.

2. The electrosurgical system of claim 1, wherein the first power delivery segment occurs during a time period of between 0.250 and 9.75 seconds.

3. The electrosurgical system of claim 1, wherein the second power delivery segment occurs during a time period of between 0.250 and 9.75 seconds.

4. The electrosurgical system of claim 1, wherein the electrosurgical generator is configured to deliver an amount of power during the first power delivery segment that will not cause any tissue trapped in the pair of jaws to reach a temperature that results in boiling of any moisture in the tissue.

5. The electrosurgical system of claim 1, wherein the electrosurgical generator is configured to deliver an amount of power during the first power delivery segment that causes any tissue trapped in the pair of jaws to desiccate.

6. The electrosurgical system of claim 1, wherein the electrosurgical generator is configured to ensure that the final power level will not cause over-desiccation of any tissue trapped in the pair of jaws.

7. The electrosurgical system of claim 1, wherein the electrosurgical generator is configured to ensure that the second power delivery segment ends when any tissue in the pair of jaws has an impedance that exceeds a predetermined value.

8. The electrosurgical system of claim 1, wherein the first power delivery segment has a shape selected from the group consisting of linear, concave, convex, and combinations thereof.

9. The electrosurgical system of claim 1, wherein the second power delivery segment has a shape selected from the group consisting of linear, concave, convex, and combinations thereof.

10. The electrosurgical system of claim 1, wherein the first power delivery segment comprises an exponential decay curve and the second power delivery segment is linear.

11. The electrosurgical system of claim 1, wherein the first power delivery segment occurs over a time period from zero to 0.750 seconds.

12. The electrosurgical system of claim 1, wherein the second power delivery segment occurs over a time period from 0.750 seconds to 4.25 seconds.

13. A method of controlling the power output from an electrosurgical generator to a vessel sealer having a pair of jaws, comprising:

providing the vessel sealer having the pair of jaws;

coupling the electrosurgical generator to the pair of jaws of the vessel sealer;

powering the electrosurgical generator to output radiofrequency energy to the vessel sealer according to a predetermined continuous power curve, wherein the predetermined continuous power curve starts with a first power delivery segment that commences at a first power level and then continuously decreases to a predetermined second, non-zero power level and a second power delivery segment that commences with the second power level and increases to and then ends at a final power level that is greater than the predetermined second, non-zero power level.

14. The method of claim 13, wherein the first power delivery segment occurs during a time period of between 0.250 and 9.75 seconds.

15. The method of claim 13, wherein the second power delivery segment occurs during a time period of between 0.250 and 9.75 seconds.

16. The method of claim 13, wherein the electrosurgical generator is configured to deliver an amount of power during the first power delivery segment that will not cause any tissue trapped in the pair of jaws to reach a temperature that results in boiling of any moisture in the tissue.

17. The method of claim 13, wherein the electrosurgical generator is configured to ensure that the second power delivery segment ends when any tissue in the pair of jaws has an impedance that exceeds a predetermined value.

* * * * *